United States Patent [19]
Tramont

[11] Patent Number: 4,880,418
[45] Date of Patent: Nov. 14, 1989

[54] OBSTETRIC SAFETY DEVICE

[76] Inventor: Charles V. Tramont, 929 Mennonite Rd., Mantua, Ohio 44255

[21] Appl. No.: 160,815

[22] Filed: Feb. 26, 1988

Related U.S. Application Data

[63] Continuation-in-part of Ser. No. 30,168, Mar. 25, 1987, abandoned, which is a continuation of Ser. No. 795,513, Nov. 6, 1985, abandoned.

[51] Int. Cl.⁴ ............................................. A61B 17/42
[52] U.S. Cl. .................................. 604/356; 128/361; 248/97; 248/99
[58] Field of Search ..................... 128/361, 352, 353; 604/356, 357; 269/322, 327; 383/38, 40; 248/99, 97, 98; 182/138, 139

[56] References Cited

U.S. PATENT DOCUMENTS

| 527,594 | 10/1894 | Dromgoole | 182/139 |
| 3,216,423 | 11/1965 | Blonsky et al. | 124/6 X |
| 3,491,973 | 1/1970 | Hartbauer et al. | 248/99 X |
| 4,221,371 | 9/1980 | Kuphal | 604/356 X |

*Primary Examiner*—Michael H. Thaler
*Attorney, Agent, or Firm*—Donald A. Bergquist

[57] ABSTRACT

This invention relates to a device to render protection to a newborn infant against being injured due to an accident in which the infant is dropped onto the floor or other solid object at or following the moment of birth in a delivery room or in a birthing room. The invention is a safety net to catch a falling newborn at or immediately after the moment of birth, in combination with a collection system for the waste body fluids incident to the birthing process whereby these fluids are collected in a disposal receptacle that is a part of the invention.

11 Claims, 5 Drawing Sheets

OBSTETRIC SAFETY DEVICE

This application is a continuation-in-part of application Ser. No. 07/030,168, filed 3/25/87, now abandoned, which is a continuation of application Ser. No. 06/795,513, filed 11/06/85 now abandoned.

BACKGROUND OF THE INVENTION

This invention relates to a device to render protection to a newborn infant against being injured due to an accident in which the infant is dropped onto the floor or other solid object at or following the moment of birth in a delivery room or in a birthing room. A significant added feature is that the waste body fluids incident to the birthing process are collected in a disposal receptacle that comprises a part of the invention.

An injury of the type at which this invention is directed may be seen as one of disastrous proportions, not only to the infant who sustains the physical injury, but as both an emotional and a financial disaster to the parents, who may seek and obtain by way of a lawsuit, recompense of tremendous proportions for the same from the attending physician or other practitioner and from the obstetrical institution involved.

It is common practice in the delivery of babies in a hospital's delivery room that the expectant mother is on a delivery table in a lithotomy position on her back with her legs elevated and separated in support devices commonly called stirrups. A significant feature of delivery tables in common use is that the horizontal portion of the table that would support the patient's legs from the buttocks downward is collapsed, rolled away, or otherwise removed to provide the attending physician or other practitioner full and convenient access to the birth canal to perform his functions.

Recent years have seen the increased use of a so-called "birthing bed", "birthing chair", or "birthing stool", in which the expectant mother is seated in a semi-reclining position with her legs flexed and separated. Thus the same problem can be seen to exist in such a birthing bed, chair, or stool as exists on a delivery table. In this patent, the term "birthing bed" shall encompass "birthing bed", "birthing chair", "birthing stool", and the like.

The physical arrangements described above present a potential hazard to the newborn in that the newborn, being coated with amniotic fluid, with vernix caseosa (a natural greasy protective skin coating), occasionally with meconium (infant feces), and with other lubricants that may have been artificially applied to the birth canal by the attending physician or other practitioner, is extremely slippery and difficult to hold, especially if it is squirming, and it is at this crucial moment that the infant stands the greatest chance of being dropped, there being no support below the infant but the hands of the attending physician or other practitioner.

A similar hazard exists in instances wherein the attention of the attending physician or other practitioner (hereinafter, the term "attendant" will encompass "attending physician" and "attending practitioner") is momentarily distracted at a crucial phase of the delivery when an expectant mother suddenly and without notice exerts a forceful push. Such distractions often occur after delivery of the infant's head and prior to delivery of the shoulders, at which time the attendant reaches for a bulb syringe from the instrument table so that he may suction the infant's mouth and nose. It is very often at this moment that the mother experiences an uncontrollable urge to push. Thus, the baby may deliver precipitously with the attendant in an unsuitable position to receive it and so the infant may fall to the floor and be injured, often severely so.

Another dangerous situation that is all too common is one in which the umbilical cord is found to be wrapped tightly one or more times around the infant's neck or shoulders. This situation is first evidenced following delivery of the head and before delivery of the shoulders and again is subject to unusually forceful uncontrollable maternal pushing that may occur while the attendant is occupied with attempts to quickly clamp, cut, and unravel the tightly-wound umbilical cord so the delivery may proceed in an uncomplicated fashion. Here again, the attendant's attention is divided between controlling the delivery and his efforts to reach for clamps and scissors from the instrument table.

Other precarious situations include: delivery of infants in breech position, especially while employing the use of forceps to deliver the aftercoming head; the use of forceps in general; encountering difficulty in carrying out the episiotomy while controlling delivery of the head during episodes of excessive maternal pushing; multiple births; unpredictable situations, such as very uncooperative mothers; and the exceptionally slippery infant who slips through the hands of an attendant who may have been without sleep for many hours, which lack of sleep is a common occurance in the practice of obstetrics.

The hazard of an infant being dropped is mostly present during "natural" deliveries, which by their very nature encourage the mother to push throughout the delivery; this pushing, hoewever, is not always well controlled and therefore problems such as those previously outlined may indeed arise.

A corrollary to "natural" deliveries is the one in which the father participates or actually does the delivery under the attendant's supervision. This scenario, along with the advent of birthing rooms, birthing beds, etc., has become quite popular and, in the process, has invited more opportunity for problems to occur at the time of delivery. In these instances, the mere presence of a safety net will relieve much of the anxiety of the attendant and the father, and, in effect, will reduce the liability the attendant encounters when he allows the father to participate in the delivery process.

Lastly to be considered are the time-honored training programs wherein medical students, interns, obstetrical residents, and midwife trainees learn the art of obstetrics. The inherent danger of dropping babies at delivery may be most acute in institutions that conduct such training. Again, the presence of a safety net will not only relieve the anxiety of the trainee and that of the resident physician doing the training, but it will also instill in the trainee an increased sense of confidence. The training institutions and all other institutions that offer obstetrical services will, by having and using the safety net, be substantially relieved of a most serious and indefensible liability.

Whatever the cause may be, a significant portion of the onus for any injury to the fallen newborn is laid upon the attending physician or other practitioner, who is already faced with burdensome and excessive premiums for insurance against malpractice claims, which premiums in 1985 were already at crisis proportions.

It is therefore the object of this invention to provide a net that is capable of being placed in a position to provide protection by catching the newborn infant, should the infant fall, without interfering with the normal functions of the attending physician or other practitioner.

It is another object of this invention to provide a net that, although it is fully capable of catching the falling infant as described, nonetheless has openings sufficient to allow relatively free passage of the fluid and some of the solid debris incidental to the birth process, such as the amniotic fluid and bits of placental tissue, feces, and blood clots, all of which are hygienically collected in a disposable flexible bag. The soiled safety net is, at the completion of the delivery, collected and enlcosed in the volume of the disposable bag, which is then closed for disposal thereof, thus preventing the body fluids and other products of conception from spilling onto the floor and becoming a potential route for the spread of disease, especially the spread of the HIV virus which is believed to be the contageous etiologic agent for AIDS (acquired immune deficiency syndrome) and which is spread via the transfer of body fluids.

It is a further object of this invention to provide a sterile and disposable net for use as above, or a sterile flexible covering for the net which can act as a replacement for the sterile "butt sheet" in current use.

It is another object of this invention to provide a supporting framework for the net described above.

DISCUSSION OF PRIOR ART

The one reference that has been found relating a net of any kind to the birthing process is found in U.S. Pat. No. 3,216,423 issued to Blonsky et al. In the Blonsky patent a pocket-shaped reception net made of strong elastic material is suspended in a position between the legs of the expectant mother to catch the newborn infant whose birth has been aided by the mother's being spun on the centrifuge device that is the subject of the invention. Such a reception net is made necessary in the Blonsky patent because the attendant is not provided the opportunity to be present on the centrifuge to receive the infant directly. In the Blonsky patent the arrival of the newborn infant in the net trips a switch to stop the machinery. A wad of cotton protects the child against too direct a contact with the upright switch-out plate. No provision is present in the Blonsky patent for the containment of the waste body fluids incident to the birthing process, nor is concern raised regarding the health care worker's contact with those potentally infectious body fluids.

SUMMARY OF THE INVENTION

Application of the simple principle of preventing injuries to the newborn infant during the birthing process is made in the form of an obstetrical safety system comprising a safety net coupled with a collection system that serves to help prevent the spread of disease via body fluids incident to the birthing process. The safety net is designed to safely cushion the newborn infant's accidental fall and allows for passage of body fluids and other materials incidental to the birthing process to pass therethrough into the closed collection system below for hygienic disposal.

The net is supported at a fixed distance from the edge of the delivery surface while its height is easily adjusted to that of the table. In the preferred embodiment, the net is made of strong polyethylene material engineered to handle the fall of weights far in excess of that of even the heaviest infant. The net itself comprises a sheet or web of material that has openings which allow body fluids and solid debris incidental to the birthing process to pass freely into a hygienic, closed collection system also made of polyethylene in the preferred embodiment. In the best mode, the only communication between the volume within the safety net and the volume within the collection system is via said openings, so a falling infant could not bypass the net and fall into the accumulated waste. The safety net and collection system are designed to not interfere with the attendant regardless of his or her preferred position during the delivery.

The obstetrical safety system is supported by a substantial, portable, freestanding, stainless steel frame that allows secure and easy attachment of the polyethylene components. It could also be supported by rods extending from the delivery table or birthing bed, which rods may slide into the structure of the table or may be adapted otherwise to receive support from the table.

The system is placed in position once the mother has been "stirrupped" so that prepping solution contaminated by use in cleansing and sterilizing her body parts may be collected in a sanitary manner and more importantly so the safety net is in position while the attendant is scrubbing and gowning himself and draping the mother in preparation for the delivery. The attendant places a specially-designed, sterile, disposable overdrape that extends under the mother's buttocks and covers the safety net, the latter portion having holes that at least roughly correspond to those in the net, thereby to provide a sterile field and yet allow the various body fluids and solid debris to pass freely into the collection area below the net. This sterile topping drape may be covered over by a second such drape if the need arises during the delivery, to keep the delivery field sterile during the birthing process.

Following delivery and repair of the episiotomy and lacerations, soiled draping from the entire potentially contaminated area is easily inserted and packaged in the collection container along with the body fluids and other products of conception. The collection container is then closed for disposal, preferably by means of a drawstring closure.

The risks involved in handling body fluids have currently taken on an ominous connotation, especially in regard to health car workers and in a hospital setting. Any means that can reduce the risk of spreading the HIV virus (believed to be the contageous etiologic agent for AIDS), which is spread via the transfer of body fluids, should be made available as soon as possible.

The heretofore time-honored floor basin at the foot of the delivery table is antiquated by today's standards. The spillage of blood and other body fluids that is present on the floor surrounding the basin following delivery is a well-known fact of life. In view of the spread of AIDS and other diseases that may be transmitted by entities in those body fluids, the cleanup, which can be formidable, entails risks of greater proportions than had previously been present before the current AIDS outbreak; risks that health care workers are not willing to take; risks that they should not have to take. Thus, the second potentially hazardous delivery room situation has been addressed and solved in a truly practical fashion in the form of the obstetrical safety system.

DETAILED DESCRIPTION OF THE INVENTION

This invention will be most easily understood by reference to the accompanying drawings, wherein like reference numbers are used to make reference to the same parts throughout the several drawings.

This invention combines a safety net for the prevention of injury to a newborn infant, should the infant fall or be dropped at the moment of birth or immediately thereafter, with a hygienic receptacle for collecting and disposing of the waste products of human conception, some of which waste products may contain viruses or other infectious agents and with which the health care workers are therefore best advised to avoid direct contact. Of special concern to health care workers in 1988 is the potential for exposure to the HIV virus.

Figure 1:
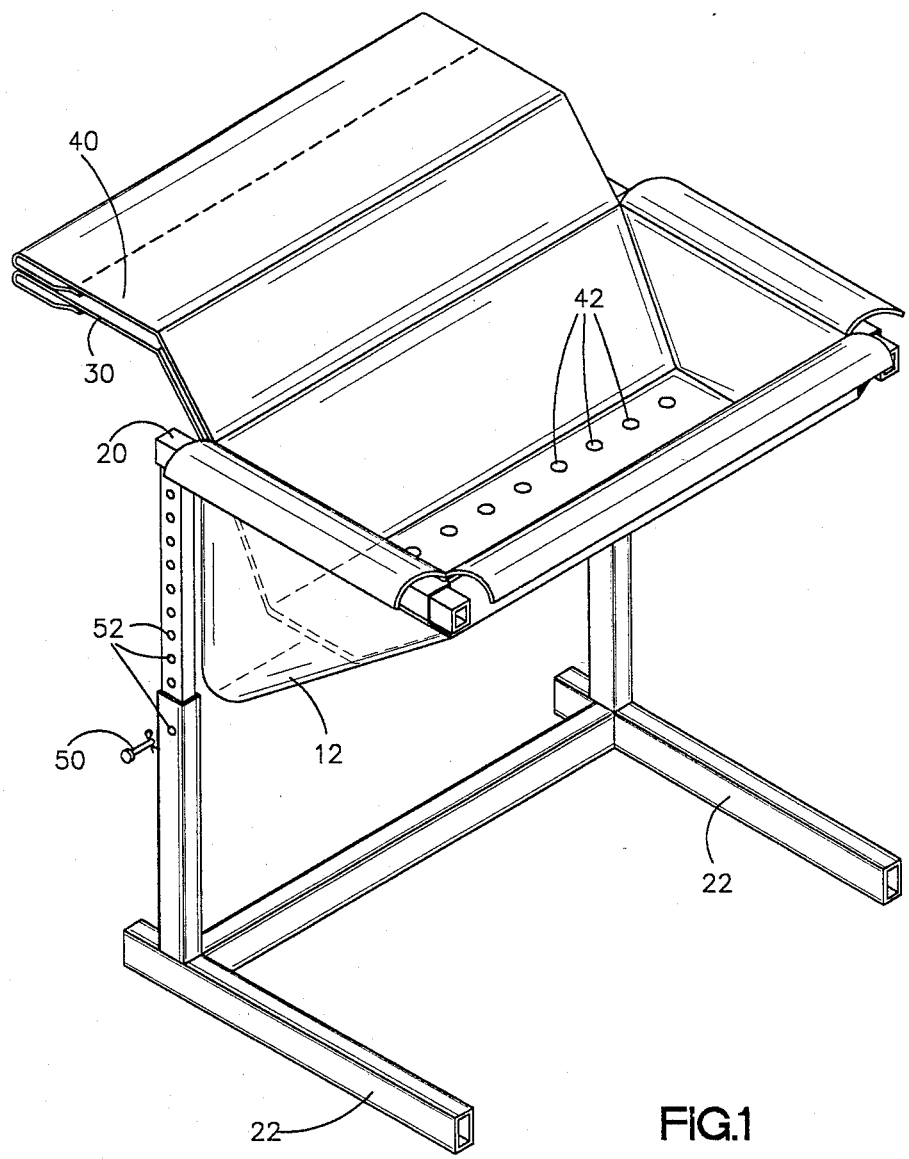
FIG. 1 shows a perspective drawing of this invention positioned on a support means as it would be used.
Figure 2:
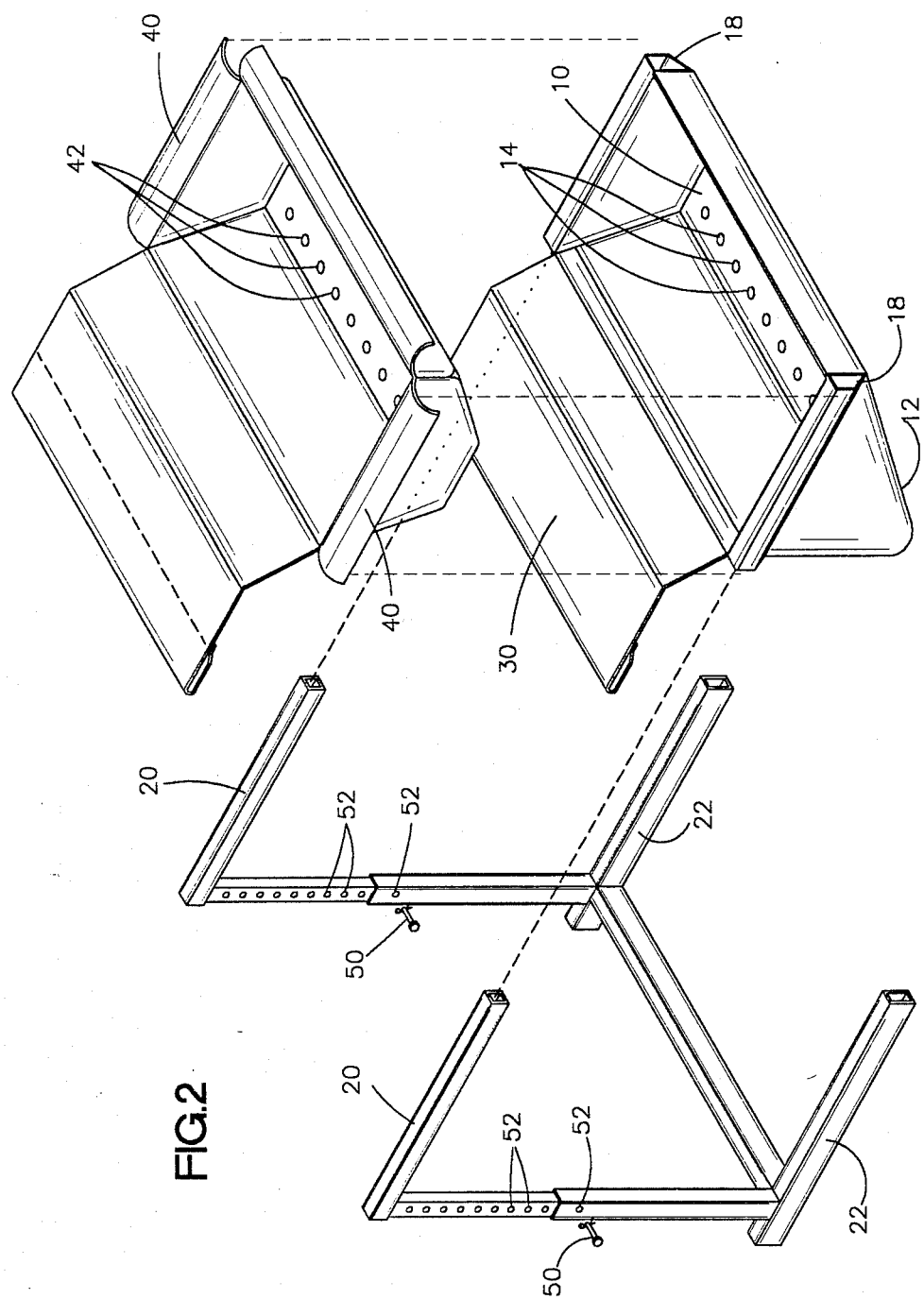
FIG. 2 shows an exploded drawing of the several parts of this invention to clearly show their separability.
Figure 5:
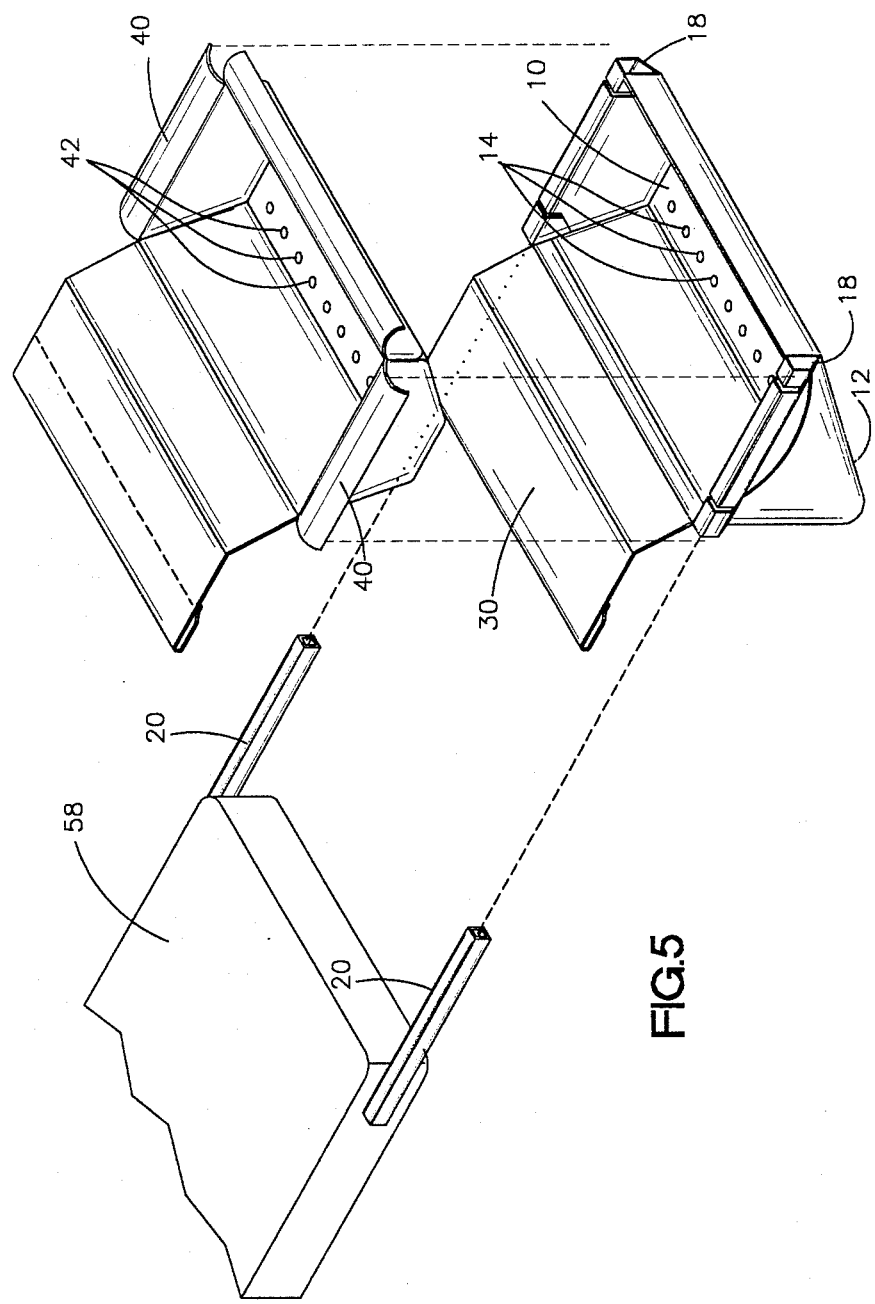
FIG. 5 shows a perspective drawing of alternative embodiments of the invention.

FIG. 1 and FIG. 2 show an example of the invention net 10 of the best mode where it is made as an integral part of the disposal receptacle 12. As shown in FIG. 5, the net 10 could also be separate from the receptacle 12, though in practice it would be used in conjunctionn with such a receptacle.

The net, though it bears that name, need not be made of any sort of netting material; indeed, in the best mode the net is made of polyethylene sheeting with holes 14 punched therethrough. The net is so called because its function is that of a safety net to catch the newborn infant should the infant fall or be dropped at the time of its delivery from the mother or immediately thereafter. The material from which it is made must retain its strength when wet with water, blood, and other liquids incident to the birthing process. The net must have openings therethrough sufficient to allow the relatively free flow of the liquids incident to the birthing process. Also incident to the birthing process are waste solids, such as fecal matter from both the mother and the infant, bits of placental tissue, and clotted blood, which must also pass through the openings in the net with relative ease.

The net is supported along at least two sides thereof. In the best mode as shown in the drawings, the support is derived by means of elongated pockets 18 on each end of the net, each of which pockets receives a horizontal elongated arm 20 that, in the best mode is a part of a free-standing support frame 22. The support means required for this invention is characterized by the absence on at least one side thereof of any rigid horizontal bracing element above the plane of the floor.

Figure 6:
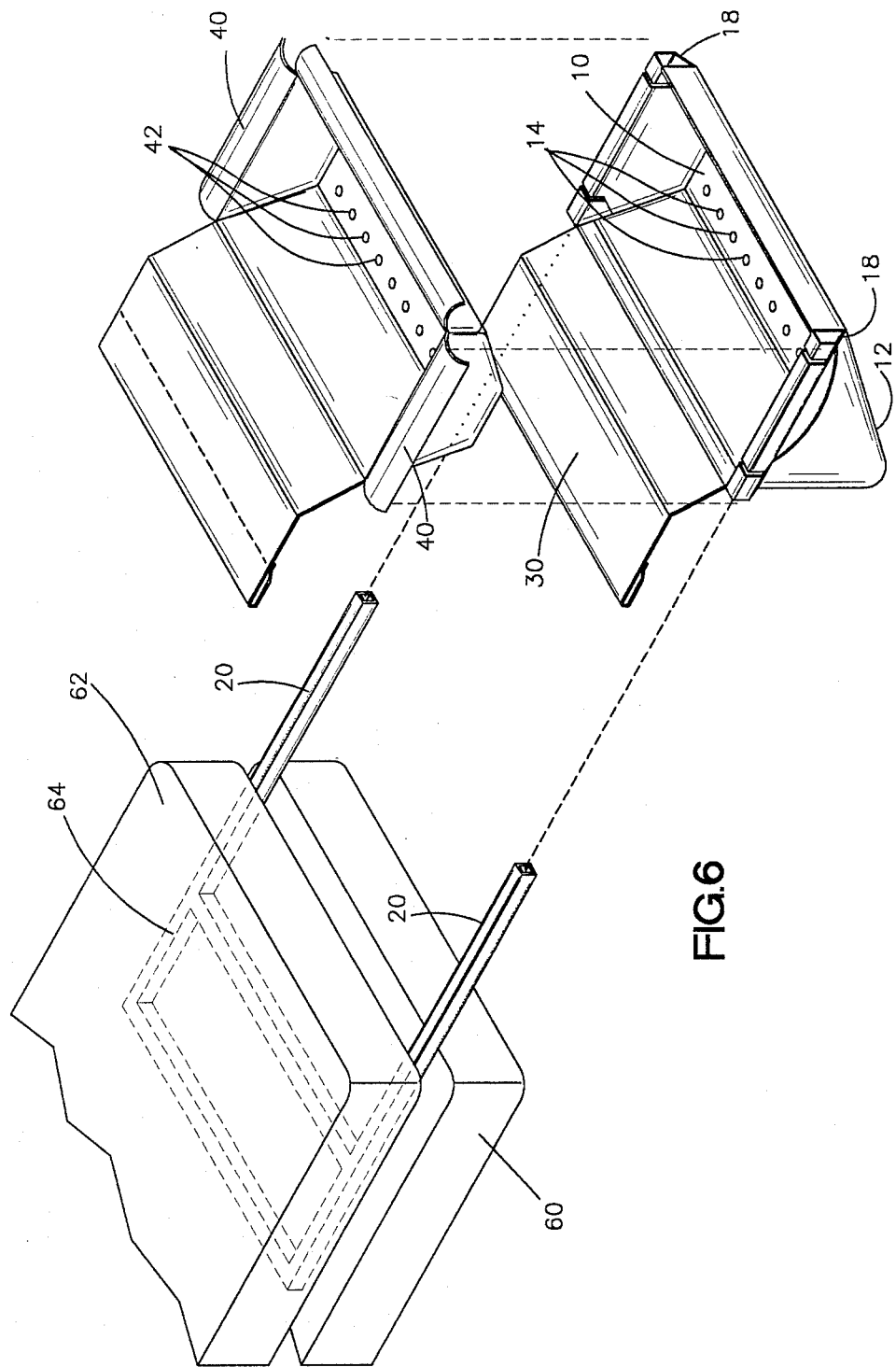
FIG. 6 shows a perspective drawing of yet another alternative embodiment of the invention.

FIG. 5 illustrates that support for the net could be obtained by means of two bars 20 adapted to attach to the delivery table 58 or birthing bed and extend therefrom in a substantially horizontal direction from the end of the table. As shown in FIG. 6, in the case of a birthing bed having a spring 60 and a mattress 62 similar to conventional beds, a support means comprising substantially parallel bars 20 mounted on a framework 64 that may be inserted between the mattress 62 and spring 60 would provide adequate support for the net.

The waste collection receptacle is, in the best mode, made as an integral part of the net. In the best mode, the waste collection receptacle includes an extended flap 30 that is to be inserted under the buttocks of the mother as she rests upon the supporting surface of the delivery table or birthing bed. This extended flap is continuous with the collection receptacle so that liquid that runs onto the extended flap is thereby directed to flow into the waste receptacle, usually through the net.

Figure 3:
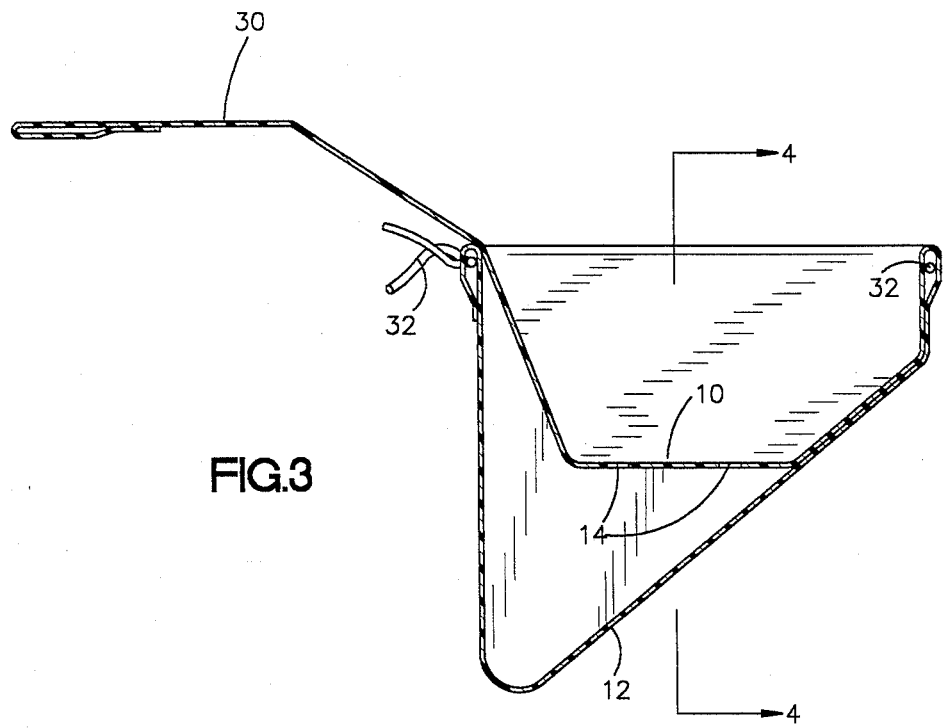
FIG. 3 shows a cross-sectional view of the combined safety net and disposal receptacle of this invention.
Figure 4:
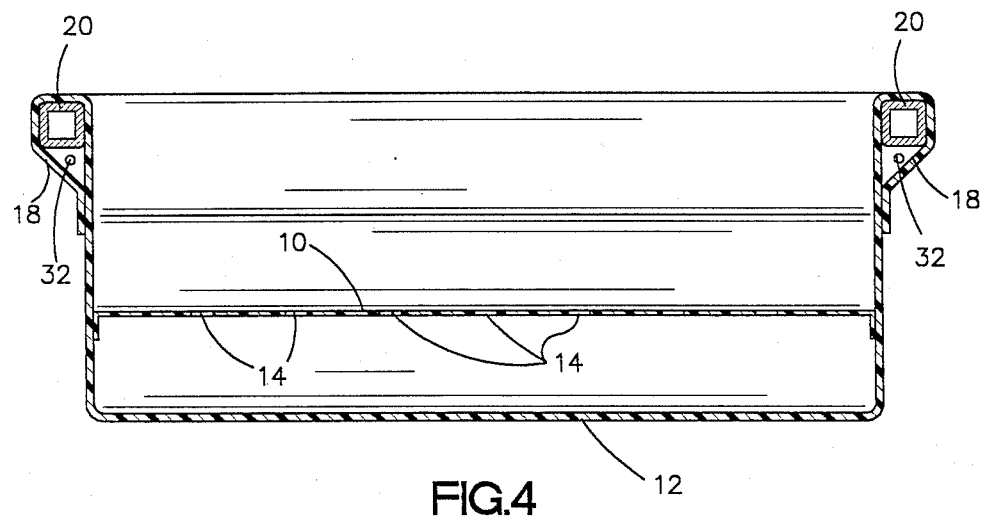
FIG. 4 shows a second cross-sectional view of the combined safety net and disposal receptacle of this invention.

Included in an elongated pocket completely encircling the opening of the collection receptacle and extending from such pocket in at least one location is a drawstring 32, visible in FIG. 3 and FIG. 4, for securely closing the opening of the receptacle. In the drawings, notably in FIG. 4, the drawstring is shown to share the elongated pockets with the support bars 20, but in practice the elongated pocket for the drawstring may be in a completely separate pocket. It should be understood that upon completion of the delivery and the repair of the episiotomy, the collection receptacle may be used for disposal of all manner of disposable articles, drapes, swabs, and the like used during the procedure. The receptacle is slid from the support means and the drawstring is pulled to create a purse-string closure of the top of the receptacle. Some added protection for the health care workers arises from the fact that, upon such closing of the receptacle, the net supports the discarded draping materials close to the closure of the receptacle, forming a somewhat absorbent barrier that helps prevent leakage therethrough of the liquid wastes contained at the bottom of the receptacle.

An alternative of some interest is the locating of the drawstring pocket several inches from the open edge of the receptacle. When closing the receptacle, the potentially contaminated edges are first folded into the receptacle and the drawstring is pulled, thereby leaving only uncontaminated edges exposed at the drawstring closure.

In practice, it is greatly to be preferred that the field in which the attendant works is sterile. To this end, the exposed parts of the mother are cleansed and made sterile by the use of a "prepping solution" and her body parts to which access by the attendant is not essential are "draped" with sterile material. So, too, the safety net and extended flap portions of the present invention would best be sterile or covered by sterile material. If the net and extended flap were installed sterile, it could easily be contaminated during the preparing of the mother or during the birthing process. In the best mode, therefore, the sterility of the net is not to be taken for granted and a sterile drape 40 for the net is provided. This drape, or "butt sheet", covers the net and the edges thereof and also covers the extended flap. The drape may be made of polyethylene or it may be made of another material, such as paper of the type presently used in surgical draping. It carries no load in the function of the safety net; its only function is to provide a sterile field in which the attendant works. This sterile drape is a part of the best mode of the present invention. If the drape becomes soiled or contaminated, it may be covered over with an additional such drape to restore the sterile field.

It is best that the sterile drape be formed to fit the safety net and cover the edges thereof and be provided with the necessary holes therethrough. In practice, any sort of sterile drape that covers the areas of immediate concern to the attendant could be used. It should be remembered, however, that relatively free passage of fluids through the safety net should be maintained, by splashing the drape if needed, so the fluids do not collect on the surface of the net where a falling infant could splash them around the room and thereby defeating the collection system.

Also shown in the figures are some features of the best mode of the present invention that are somewhat less functional and less essential than those that have been thus far described. The support means is preferably adjustable in height, as is shown especially in FIG. 2, wherein removable pins 50 function cooperatively with mating sets of holes 52 in the two-piece vertical portion of the support device. In addition, the support device is designed to have no horizontal bracing at the edge adjacent the attendant during use thereof. There is no barrier of any sort on the floor to obstruct the attendant, regardless of the position the attendant prefers to assume during either the delivery or during the repair of the episiotomy; the objectionable floor basin of prior art is no longer necessary.

Although a variety of specific arrangements have been recited in this specification, it will be obvious to one skilled in the art to produce a product that may deviate from these specifics and yet remain within the spirit of this invention. Specifically, the shape of the receptacle and of the net are easily changed and those presented herein should in no way be considered restrictive. It is the intent of the applicant that such deviations be included within the scope of the present invention.

I claim:

1. In an environment designed for facilitating a practitioner's assisting a pregnant woman in the delivery of her child, which environment comprises a first support means that supports the woman at a convenient and stable elevation above the floor, which first support means may be a delivery table or birthing bed, birthing chair, birthing stool, for examples; the improvement being an apparatus comprising a substantially planar safety net with openings through the thickness thereof in combination with a flexible baglike hygienic disposal receptacle having an opening wherein said net and said receptacle are releasably supported by means of and in combination with a second support means so the net is in a substantially horizontal orientation within the opening of said disposal receptacle, said disposal receptacle being capable of collecting and holding the wastes incident to the birthing process.

2. The combination described in claim 1 wherein there extends from said net an imperforate rectangular flap along one edge thereof, which flap is useful in anchoring said net by placing said flap between the buttocks of said woman and the surface of said first support upon which said buttocks rest, which flap also serves the purpose of guiding body fluids and other fluids incident to the birthing process into said net and disposal receptacle.

3. The combination described in claim 1 wherein said second support means is characterized by the absence on at least one side thereof of any rigid horizontal bracing elements.

4. The combination described in claim 1 wherein said net and said disposal receptacle are of unitary one-piece construction.

5. The combination described in claim 1 wherein said net and said disposal receptacle are separate units designed to be used in said cooperative combination.

6. The combination described in claim 1 wherein said disposal receptacle includes a drawstring closure that provides for closing the opening thereof.

7. The combination described in claim 6 wherein said drawstring closure is positioned away from the opening of said disposal receptacle so that the edges of said receptacle forming said opening may be folded into the receptacle before the drawstring is pulled, thereby enclosing within the receptacle potentially contaminated surfaces surrounding the opening thereof.

8. The combination described in claim 1 in further combination with a covering sterile drape therefor, which drape is characterized by having openings through the thickness thereof, which openings may align with openings present in said safety net.

9. The combination described in claim 8 wherein said sterile drape, in addition to covering the net, extends as a rectangular flap along one edge thereof, which flap is useful in anchoring said drape by placing said flap between the buttocks of said woman and the surface of said first support upon which said buttocks rest, and which flap may also help in guiding body fluids and other fluids incident to the birthing process into said net and disposal receptacle.

10. The combination described in claim 1 wherein said second support means comprises two rods adapted to be attached to and supported by said first support means in a substantially horizontal orientation and substantially parallel to one another.

11. The combination described in claim 1 wherein said first support is a birthing bed comprising a mattress and wherein said second support means comprises two rods in substantially parallel juxtaposition mounted in a substantially horizontal orientation by means of a framework that is adapted to be inserted under said mattress of said birthing bed.

* * * * *